(12) United States Patent
Wang et al.

(10) Patent No.: US 8,496,688 B2
(45) Date of Patent: Jul. 30, 2013

(54) FLEXIBLE SPINE FIXING STRUCTURE

(75) Inventors: Jaw-Lin Wang, Taipei (TW); Dar-Ming Lai, Taipei (TW); Shan-Chang Chueh, Taipei (TW); Chih-Ming Wu, Hsinchu (TW); Pei-Yu Peng, Toufen Township, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 176 days.

(21) Appl. No.: 12/860,066

(22) Filed: Aug. 20, 2010

(65) Prior Publication Data
US 2011/0160771 A1 Jun. 30, 2011

(30) Foreign Application Priority Data

Dec. 31, 2009 (TW) .............................. 98146265 A (51) Int. Cl.
*A61B 17/70* (2006.01)
(52) U.S. Cl.
USPC .......................................... 606/249; 606/250
(58) Field of Classification Search
USPC ..................... 606/246–249; 623/17.11–17.16
See application file for complete search history.

(56) References Cited

U.S. PATENT DOCUMENTS

| | | | |
|---|---|---|---|
| 5,470,333 A | 11/1995 | Ray | |
| 5,486,176 A | 1/1996 | Hildebrand et al. | |
| 5,531,746 A | 7/1996 | Errico et al. | |
| 5,545,164 A | 8/1996 | Howland | |
| 5,558,674 A | 9/1996 | Heggeness et al. | |
| 6,283,967 B1 | 9/2001 | Troxell et al. | |
| 6,524,315 B1 | 2/2003 | Selvitelli et al. | |
| 6,547,790 B2 | 4/2003 | Harkey, III et al. | |
| 6,902,565 B2 | 6/2005 | Berger et al. | |
| 2003/0191470 A1 | 10/2003 | Ritland | |
| 2005/0119657 A1 | 6/2005 | Goldsmith | |
| 2005/0228378 A1 | 10/2005 | Kalfas et al. | |
| 2006/0129239 A1* | 6/2006 | Kwak ........................ 623/17.13 | |
| 2006/0149230 A1* | 7/2006 | Kwak et al. ..................... 606/61 | |
| 2006/0149239 A1 | 7/2006 | Winslow et al. | |
| 2006/0149254 A1 | 7/2006 | Lauryssen et al. | |
| 2006/0149272 A1 | 7/2006 | Winslow et al. | |
| 2006/0149289 A1 | 7/2006 | Winslow et al. | |

(Continued)

OTHER PUBLICATIONS

TW Office Action (Dated Oct. 16, 2012).

(Continued)

*Primary Examiner* — Jan Christopher Merene
*Assistant Examiner* — Michelle C Eckman
(74) *Attorney, Agent, or Firm* — McClure, Qualey & Rodack, LLP (57) ABSTRACT

A flexible spine fixing structure for fixing to a first vertebra and a second vertebra includes a first flexible element and a second flexible element. The first flexible element includes a first flexible part, a first fixing part and a second fixing part. The first fixing part and the second fixing part are respectively connected to two ends of the first flexible part and used for fixing to the first vertebra, and the first flexible part includes a first through hole and a second through hole. The second flexible element includes a second flexible part, a third fixing part and a fourth fixing part. The third fixing part and the fourth fixing part are respectively connected to two ends of the second flexible part and used for fixing to the second vertebra. The second flexible part is disposed by penetrating through the first through hole and the second through hole.

15 Claims, 4 Drawing Sheets

U.S. PATENT DOCUMENTS

| | | | |
|---|---|---|---|
| 2006/0149373 A1 | 7/2006 | Winslow et al. | |
| 2006/0149374 A1 | 7/2006 | Winslow et al. | |
| 2006/0241597 A1 | 10/2006 | Mitchell et al. | |
| 2006/0247632 A1 | 11/2006 | Winslow et al. | |
| 2006/0247633 A1 | 11/2006 | Winslow et al. | |
| 2006/0247650 A1 | 11/2006 | Yerby et al. | |
| 2006/0264939 A1 | 11/2006 | Zucherman et al. | |
| 2006/0271046 A1* | 11/2006 | Kwak et al. | 606/61 |
| 2006/0276794 A1* | 12/2006 | Stern | 606/69 |
| 2006/0282077 A1* | 12/2006 | Labrom et al. | 606/61 |
| 2007/0016196 A1 | 1/2007 | Winslow et al. | |
| 2007/0016218 A1 | 1/2007 | Winslow et al. | |
| 2007/0123863 A1 | 5/2007 | Winslow et al. | |
| 2007/0123872 A1* | 5/2007 | Brockmeyer et al. | 606/61 |
| 2007/0162001 A1* | 7/2007 | Chin et al. | 606/61 |
| 2007/0233088 A1* | 10/2007 | Edmond | 606/61 |
| 2007/0244483 A9 | 10/2007 | Winslow et al. | |
| 2007/0282339 A1 | 12/2007 | Schwab | |
| 2008/0033433 A1* | 2/2008 | Implicito | 606/61 |
| 2008/0058818 A1 | 3/2008 | Schwab | |
| 2008/0269804 A1* | 10/2008 | Holt | 606/254 |
| 2009/0163953 A1 | 6/2009 | Biedermann et al. | |
| 2009/0259256 A1 | 10/2009 | Miller | |
| 2009/0264931 A1 | 10/2009 | Miller et al. | |
| 2011/0152932 A1* | 6/2011 | Wang et al. | 606/246 |
| 2012/0016417 A1* | 1/2012 | Druma | 606/246 |

OTHER PUBLICATIONS

Non-Final Office Action in U.S. Appl. No. 13/309,943 dated Mar. 26, 2013.

* cited by examiner

FLEXIBLE SPINE FIXING STRUCTURE

This application claims the benefit of Taiwan application Serial No. 98146265, filed Dec. 31, 2009, the subject matter of which is incorporated herein by reference.

BACKGROUND

1. Technical Field

The disclosure relates in general to a flexible spine fixing structure, and more particularly to a flexible spine fixing structure for fixing to two or more vertebras.

2. Description of the Related Art

Normally, there are various methods to fix vertebras of a spine. One of them is to fix a number of vertebras by transverse fixing plates and then fix the fixing plates together by a longitudinal rigid structure. Another fixing structure is composed of two vertebral plates and screws. Each of the vertebral plates has a hole of a fixed angle, and the vertebral screws penetrate two vertebras through the holes to fix the two vertebras.

However, no matter which method is used, the fixed spine loses its mobility and thus the patient receiving the surgery cannot move his/her spine, such as to bend forwards or backwards. Besides, when the fixed vertebras cannot move for a long time, they will gradually fuse into a single vertebra to lose mobility forever and result in fast degeneration of neighboring vertebras.

SUMMARY

The disclosure is directed to a flexible spine fixing structure. Through its flexibility, the fixed vertebras can still move, thereby providing the spine of the patient with higher mobility, reducing discomfort of the patient after the surgery and avoiding spine degeneration.

According to a first embodiment of the present disclosure, a flexible spine fixing structure for fixing to a first vertebra and a second vertebra is provided. The flexible spine fixing structure includes a first flexible element and a second flexible element. The first flexible element includes a first flexible part, a first fixing part and a second fixing part. The first fixing part and the second fixing part are connected to two ends of the first flexible part respectively and are used for fixing to the first vertebra, and the first flexible part includes a first through hole and a second through hole. The second flexible element includes a second flexible part, a third fixing part and a fourth fixing part. The third fixing part and the fourth fixing part are connected to two ends of the second flexible part respectively and are used for fixing to the second vertebra. The second flexible part is disposed by penetrating through the first through hole and the second through hole.

According to a second embodiment of the present disclosure, a flexible spine fixing structure for fixing to a first vertebra and a second vertebra is provided. The flexible spine fixing structure includes a first flexible element, a second flexible element and a shaft. The first flexible element includes a first connecting part, a first flexible part, a second flexible part, a first fixing part and a second fixing part. One end of the first flexible part and one end of the second flexible part are connected to two opposite ends of the first connecting part respectively, the first fixing part and the second fixing part are connected to the other end of the first flexible part and the other end of the second flexible part respectively and are used for fixing to the second vertebra, the first connecting part has an indent. The second flexible element includes a second connecting part, a third flexible part, a fourth flexible part, a third fixing part and a fourth fixing part. One end of the third flexible part and one end of the fourth flexible part are connected to two opposite ends of the second connecting part respectively, the third fixing part and the fourth fixing part are connected to the other end of the third flexible part and the other end of the fourth flexible part respectively and are used for fixing to the first vertebra, the second connecting part has a first through hole. The shaft is disposed by penetrating the indent and the first through hole.

The above and other embodiment of the disclosure will become better understood with regard to the following detailed description of the non-limiting embodiment(s). The following description is made with reference to the accompanying drawings.

DETAILED DESCRIPTION

First Embodiment

Figure 1:
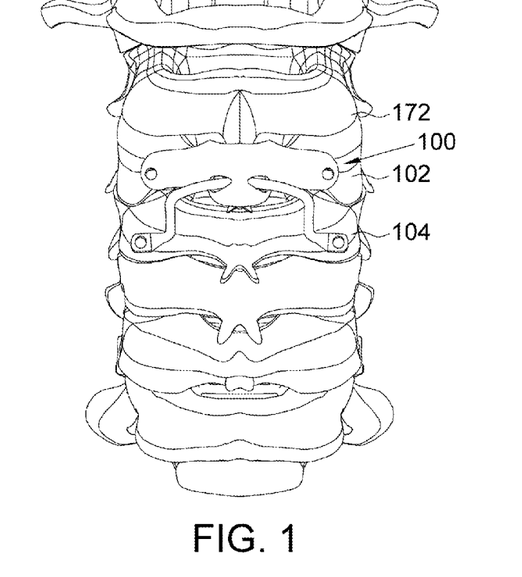
FIG. 1 is a schematic diagram of the flexible spine fixing structure configured on vertebras according to a first embodiment of the disclosure.

Referring to FIG. 1, a schematic diagram of the flexible spine fixing structure configured on vertebras according to a first embodiment of the disclosure is shown. The flexible spine fixing structure 100 is for fixing to a first vertebra 102 and a second vertebra 104, which are adjacent to each other. The first vertebra 102 and the second vertebra 104 are not limited to specific vertebras and can be any two vertebras of a spine, such as two vertebras of a cervical spine, a thoracic spine or a lumbar spine.

Figure 2:
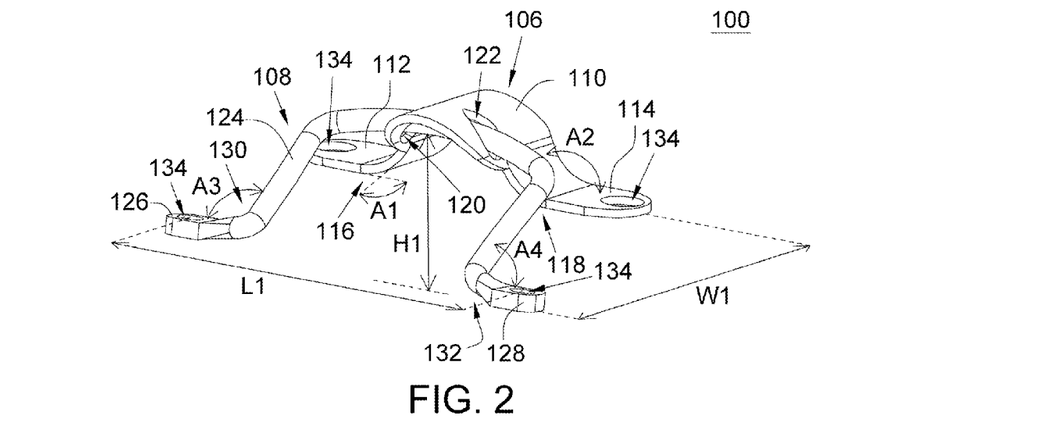
FIG. 2 is a schematic diagram of the flexible spine fixing structure of FIG. 1.

Referring to FIG. 2, a schematic diagram of the flexible spine fixing structure of FIG. 1 is shown. The flexible spine fixing structure 100 includes a first flexible element 106 and a second flexible element 108. The first flexible element 106 includes a first flexible part 110, a first fixing part 112 and a second fixing part 114. The first fixing part 112 and the second fixing part 114 are connected to a first end 116 and a second end 118 of the first flexible part 110 respectively and are used for fixing to the first vertebra 102. The first flexible part 110 has a first through hole 120 and a second through hole 122.

Each of the first fixing part 112, the second fixing part 114, the third fixing part 126 and the fourth fixing part 128 has a through hole 134. A number of fixing elements, such as screws (not shown in the figure) are used to penetrate through the through holes to lock the first fixing part 112, the second fixing part 114, the third fixing part 126 and the fourth fixing part 128 onto the first vertebra 102 and the second vertebra 104.

In another example, the first fixing part 112, the second fixing part 114, the third fixing part 126 and the fourth fixing part 128 each can also be a board having a through hole, and are, for example, fixed to the first flexible part 110 and the second flexible part 124 by welding.

The second flexible element 108 includes a second flexible part 124, a third fixing part 126 and a fourth fixing part 128. The third fixing part 126 and the fourth fixing part 128 are connected to a third end 130 and a fourth end 132 of the second flexible part 124 respectively and are used for fixing to the second vertebra 104. The second flexible part 124 penetrates the first through hole 120 and the second through hole 122.

The second flexible part 124 is directly connected to the first flexible part 110 such that the whole flexible spine fixing structure 100 has flexibility. That is, after the flexible spine fixing structure 100 is fixed to the vertebras, the fixed vertebras can still move. Therefore, the patient can still bend his/her body forwards or backwards or turn his/her body left or right to have a higher mobility and lower discomfort after surgery, and spine degeneration can be avoided.

The first flexible part 110 and the second flexible part 124 of the embodiment can achieve the effect of flexibility by way of selecting proper appearance, materials, a cross-sectional shape or other parameters. In the following description, the structure of the first flexible part 110 and the second flexible part 124 is illustrated in detail.

Each of the first flexible part 110 and the second flexible part 124 can have a shape of an arc. An included angle A1 between the first fixing part 112 and the first flexible part 110, an included angle A2 between the second fixing part 114 and the first flexible part 110, an included angle A3 between the third fixing part 126 and the second flexible part 124 and an included angle A4 between the fourth fixing part 128 and the second flexible part 124 are all obtuse angles. Preferably but not limited thereto, the obtuse angle is between 120 and 150 degrees. By doing so, the first flexible part 110 and the second flexible part 124 can have flexibility such that the two fixed vertebras can still move.

Besides, each of the first flexible part 110 and the second flexible part 124 can have a cross-sectional shape of a rectangle, a circle or an ellipse and have an appearance of being flat or long and thin in order that the first flexible part 110 and the second flexible part 124 can have the flexibility.

The first flexible part 110 and the second flexible part 124 can be made of metal, polymer, flexible materials, elastic materials or combination thereof. For example, the metal may be realized by bio-compatible metal, stainless steel, memory alloy or a metal containing titanium such as pure titanium or titanium alloy. The polymer may be realized by polyether ether ketone (PEEK), polytetrafluoroethylene (PTFE, that is Teflon) or polyethylene terephthalate (PET).

The first flexible element 106 can be manufactured by way of integrally formed in one piece, such as injection molding or plate bending. The second flexible element 108 is made by the same way as the first flexible element 106, and thus any detail is unnecessary to be given here.

Furthermore, metal wires can be embedded in the above flexible parts. For example, in another example, if the first flexible part 110 is made of polytetrafluoroethylene having soft texture, a metal wire (not shown in the figure) can be embedded in the first flexible part 110 to increase rigidity, elasticity and flexibility of the first flexible part 110. Of course, it the second flexible part 124 is also made of soft-texture material, the same processing can be done to the second flexible part 124.

Moreover, the height H1 of the fixing part relative to a top of the flexible part, the interval L1 between the through hole 134 of the third fixing part 126 and the through hole 134 of the fourth fixing part 128 and the interval W1 between the through hole 134 of the fourth fixing part 128 and the through hole 134 of the second fixing part 114 can be suitably designed such that the flexible spine fixing structure 100 does not interfere with the vertebras. For example, according to a scale of a normal vertebra, the height H1 is between 0 mm and 25 mm, the interval L1 is between 30 mm and 60 mm, and the interval W1 is between 10 mm and 25 mm.

The height H1 can be used to prevent the flexible spine fixing structure 100 from interfering with the spinous process or spinal cord. Although the height H1 is exemplified to be a distance of the fourth fixing part 128 from the second flexible part 124, the height H1 can also be a distance of the third fixing part 126 from the second flexible part 124.

The scale ranges of the above height H1, intervals L1 and W1 are not used to limit the embodiment, the actual scale can be designed based on a scale of the actual spine under surgery. That is, the flexible spine fixing structure 100 of the embodiment can be manufactured to fit the spines having different scales.

Second Embodiment

Figure 3:
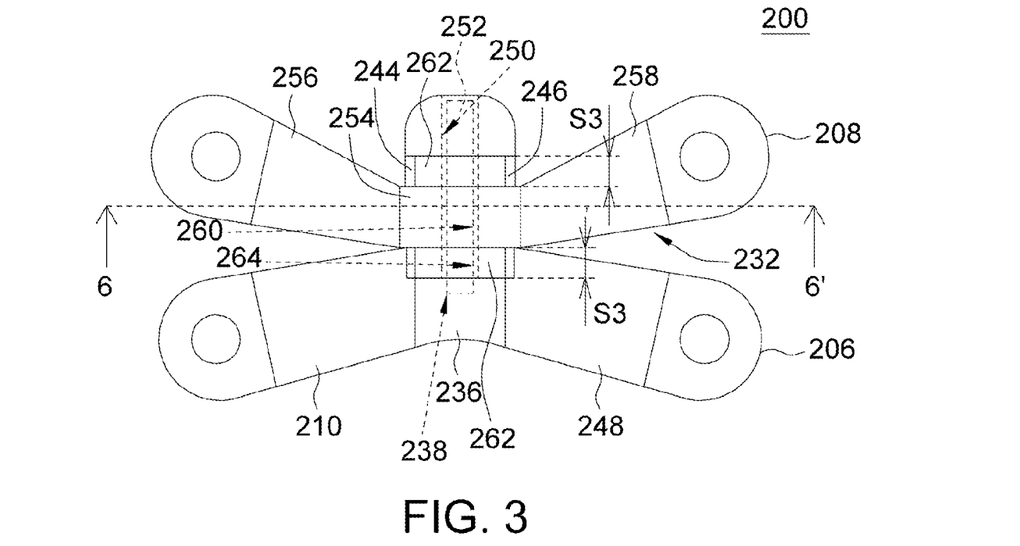
FIG. 3 is a schematic diagram of the flexible spine fixing structure according to the second embodiment of the disclosure.

Referring to FIG. 3, a schematic diagram of the flexible spine fixing structure according to the second embodiment of the disclosure is shown. The flexible spine fixing structure 200 is for fixing to the first vertebra 102 and the second vertebra 104.

The flexible spine fixing structure 200 includes a first flexible element 206, a second flexible element 208, a shaft 252 and two spacers 262. The shaft 252 is disposed by penetrating the first flexible element 206, the second flexible element 208 and the spacers 262 to prevent the first flexible element 206, second flexible element 208 and spacers 262 departing from each other.

The shaft 252 is a flexible rod and can be made of bio-compatible elastic rope, polymer, metal or other flexible or elastic material or combination thereof.

The first flexible element 206 and the second flexible element 208 can be made of metal, polymer, flexible materials, elastic materials or combination thereof. For example, the metal may be realized by bio-compatible metal, stainless steel, memory alloy or a metal containing titanium such as pure titanium or titanium alloy. The polymer may be realized by polyether ether ketone (PEEK), polytetrafluoroethylene (PTFE, that is Teflon) or polyethylene terephthalate (PET).

Owing that the first flexible element 206, the second flexible element 208, the shaft 252 and the two spacers 262 have flexibility, the whole spine fixing structure 200 has flexibility. To give a further description, when the flexible spine fixing structure 200 is fixed to the vertebras, the fixed vertebras can still move, and thus the patient can still bend his/her body forwards or backwards or turn his/her body left or right to have a higher mobility and lower discomfort after surgery and the spine degeneration can be avoided.

In the following description, the structure of the flexible spine fixing structure 200 is illustrated in detail.

Figure 4:
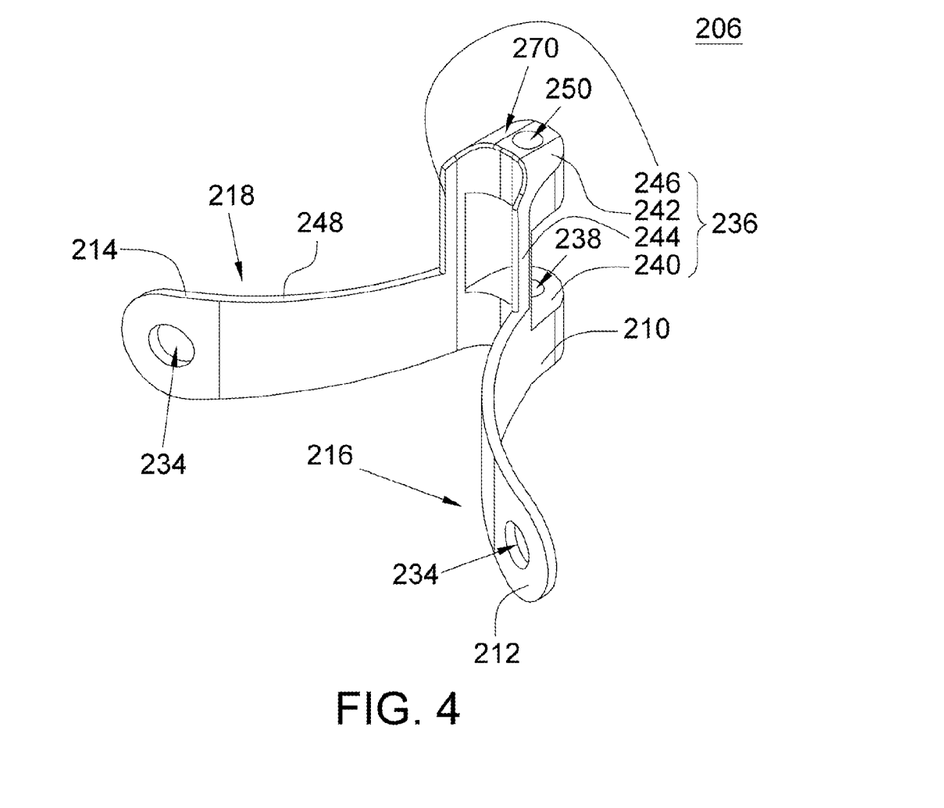
FIG. 4 is a schematic diagram of the first flexible element of FIG. 3.

FIG. 4 is a schematic diagram of the first flexible element 206 of FIG. 3. Referring to FIGS. 3 and 4 at the same time, the first flexible element 206 includes a first connecting part 236, a first flexible part 210, a second flexible part 248, a first fixing part 212 and a second fixing part 214. One end of the first flexible part 210 and one end of the second flexible part 248 are respective connected to two opposite ends of the first connecting part 236. The first fixing part 212 and the second fixing part 214 are connected to a first end 216 of the first flexible part 210 and a second end 218 of the second flexible part 248 respectively and are used for fixing to the second vertebra 104 of FIG. 1.

To give a further description, each of the first fixing part 212 and the second fixing part 214 has a through hole 234. These through holes 234 are for a number of fixing elements, such as screws (not shown in the figure) to penetrate through so as to lock the first fixing part 212 and the second fixing part 214 onto the second vertebra 104.

The first flexible element 206 can be manufactured by integrally formed in one piece, such as injection molding or plate bending.

In another example, the first flexible part 210, the second flexible part 248, the first fixing part 212 and the second fixing part 214 can be manufactured individually. For example, the first fixing part 212 and the second fixing part 214 each can also be a board having a through hole (not shown in the figure), and are fixed to the first flexible part 210 and the second flexible part 248 by welding.

The first connecting part has an indent 238, and the shaft 252 can be disposed in the indent 238. The indent 238 can be a blind hole or a through hole. In the embodiment, the indent 238 is exemplified by a blind hole for illustration.

As shown in FIG. 4, the first connecting part 236 includes a first connecting piece 240, a second connecting piece 242, a first beam 244 and a second beam 246. The first beam 244 and the second beam 246 are disposed in parallel to each other and connected to the first connecting piece 240 and the second connecting piece 242. The indent 238, the first flexible part 210 and the second flexible part 248 are formed on the first connecting piece 240. The second connecting piece 242 has a second through hole 250 and one end of the shaft 252 penetrates the second through hole 250 to be disposed in the indent 238.

Besides, the side surface 270 of the second connecting piece 242 can block an adjacent upper vertebra, such as the third vertebra 172 neighboring the first vertebra 102 in FIG. 1. The second connecting piece 242 has an effect of supporting the third vertebra 172, sharing stress for the vertebra 102 and maintaining a height position of the vertebra 102.

Figure 5:
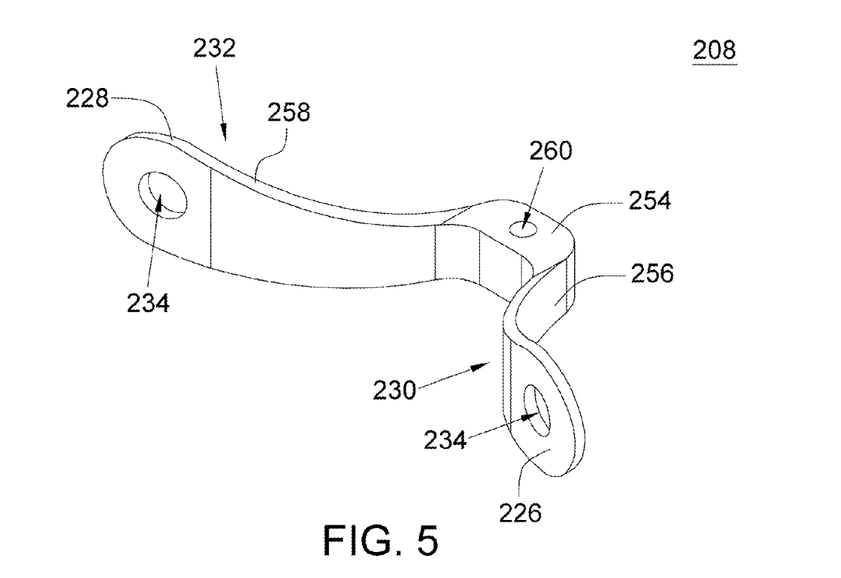
FIG. 5 is a schematic diagram of the second flexible element of FIG. 3.

FIG. 5 is a schematic diagram of the second flexible element 208 of FIG. 3. Referring to FIGS. 3 and 5 at the same time, the second flexible element 208 includes a second connecting part 254, a third flexible part 256, a fourth flexible part 258, a third fixing part 226 and a fourth fixing part 228. One end of the third flexible part 256 and one end of the fourth flexible part 258 are connected to two opposite ends of the second connecting part 254 respectively. The third fixing part 226 and the fourth fixing part 228 are connected to a third end 230 of the third flexible part 256 and a fourth end 232 of the fourth flexible part 258 respectively and used for fixing to the first vertebra 102 of FIG. 1. The second connecting part 254 has a first through hole 260 and the shaft 252 penetrates the first through hole 260.

Each of the third fixing part 226 and the fourth fixing part 228 has a through 234. The through holes 234 are for a number of fixing elements, such as screws (not shown in the figure), to penetrate through so as to lock the third fixing part 226 and the fourth fixing part 228 onto the first vertebra 102.

The second flexible element 208 can be manufactured by integrally formed in one piece, such as injection molding or plate bending.

In another example, the third flexible part 256, the fourth flexible part 258, the third fixing part 226 and the fourth fixing part 228 can be manufactured individually. For example, the third fixing part 226 and the fourth fixing part 228 each can also be a board having a through hole, and can be fixed to the third flexible part 256 and the fourth flexible part 258 by welding.

Figure 6:
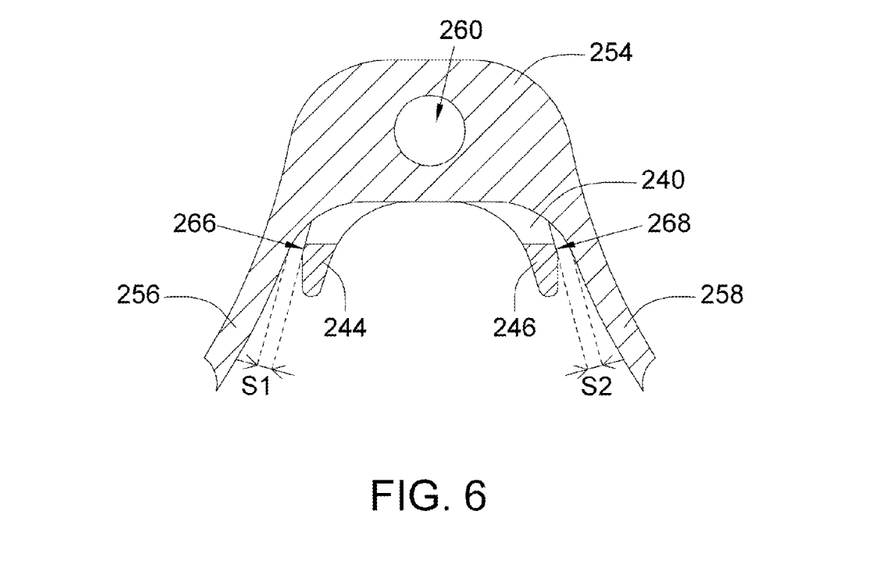
FIG. 6 is a cross-sectional diagram of the flexible spine fixing structure of FIG. 3 along a line 6-6'.

Referring to FIG. 6, a cross-sectional diagram of the flexible spine fixing structure of FIG. 3 along a line 6-6' is shown. The first beam 244 has a first side surface opposite to the third flexible part 256, and the first side surface 266 is separated from the third flexible part 256 by a first interval S1 . The second beam 246 has a second side surface 268 opposite to the fourth flexible part 258, and the second side surface 268 is separated from the fourth flexible part 258 by a second interval S2. The first interval S1 and the second interval S2 are used to provide sufficient space for motion of the second flexible element 208 such that the vertebras fixed by the third fixing part 226 and the fourth fixing part 228 can have higher mobility, wherein each of the first interval S1 and the second interval S2 is about 0.4 mm.

Further, the first side surface 266 and the second side surface 268 also have the effect of blocking the second flexible element 208. For example, when the second flexible element 208 turns to contact the first side surface 266, the first side surface 266 blocks the second flexible element 208 from continuing to turn. Therefore, the over-large rotation of the second flexible element 208 can be constrained to avoid spine injury due to unduly exercise.

Figure 7:
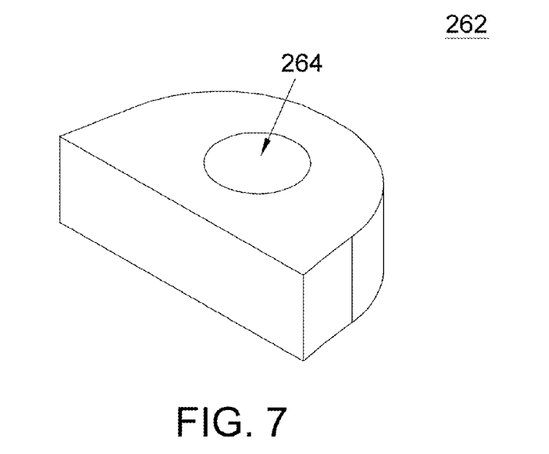
FIG. 7 is a schematic diagram of the spacer of FIG. 3.

FIG. 7 is a schematic diagram of the spacer of FIG. 3. Referring to FIGS. 3 and 7, the first connecting part 236 is separated from the second connecting part 254 by third intervals S3, two spacers 262 are disposed in the third interval S3. In the embodiment, the two spacers 262 are disposed at two opposite ends of the second connecting part 254 respectively and roughly fill up the gap between the first connecting part 236 and the second connecting part 254, thereby preventing tissues of the human body from being incautiously clapped into the above gap.

The spacers 262 can interfere or cooperate in a lessen or medium extent with the second connecting part 254, the first connecting piece 240 and the second connecting piece 242, which depends on the real situation in an actual application and is not limited in the embodiment.

Each of the spacer 262 has a third through hole 264. The shaft 252 penetrates the second through hole 250, the third through hole 264 and the first through hole 260 and is disposed in the indent 238, as shown in FIG. 3.

In the embodiment, an outer diameter of the shaft 252 is smaller than inner diameters of the first through hole 260, the second through hole 250 and the third through hole 264, and an outer diameter of the shaft 252 is larger than an inner diameter of the indent 238 such that the shaft 252 can penetrate the first through hole 260, the second through hole 250 and the third through hole 264 to be fixed into the indent 238, as shown in FIG. 3 to prevent the shaft 252 falling off and the first flexible element 206, the second flexible element 208 and the spacers 262 separating from each other.

Owing that the outer diameter of the shaft 252 is smaller than the inner diameters of the first through hole 260, the second through hole 250 and the third through 264, a gap (not shown in the figure) among the shaft 252, the first through hole 260, the second through hole 250 and the third through hole 264 is formed to provide a space for flexible deformation of the first flexible element 206 and the second flexible element 208. Therefore, the second flexible element 208 can move relative to the shaft 252.

Although the outer diameter of the shaft 252 is exemplified to be smaller than the inner diameters of the first through hole 260, the second through hole 250 and the third through hole 264 for illustration in the embodiment, the disclosure is not limited thereto. In another example, the outer diameter of the shaft 252 can be larger than the inner diameter of one of the first through hole 260, the second through hole 250 and the third through hole 264. Under this situation, the inner diameter of the indent 238 can be larger than the outer diameter of the shaft 252.

Although the shaft 252 is exemplified to have flexibility in the embodiment, in another example, the shaft 252 can also be a rigid shaft. If the shaft 252 is a rigid shaft, preferably, the outer diameter of the shaft 252 is smaller than the inner diameters of the first through hole 260, the second through hole 250 and the third through hole 264 such that the shaft 252 and the through holes form a gap. The gap provides a space for flexible deformation of the first flexible element 206 and the second flexible element 208.

The first flexible part 210, the second flexible part 248, the third flexible part 256 and the fourth flexible part 258 can achieve the effect of flexibility by way of selecting proper appearance, materials, a cross-sectional shape or other parameters in the embodiment. In the following description, the structures of the first flexible part 210, the second flexible part 248, the third flexible part 256 and the fourth flexible part 258 are given in detail.

Figure 8:
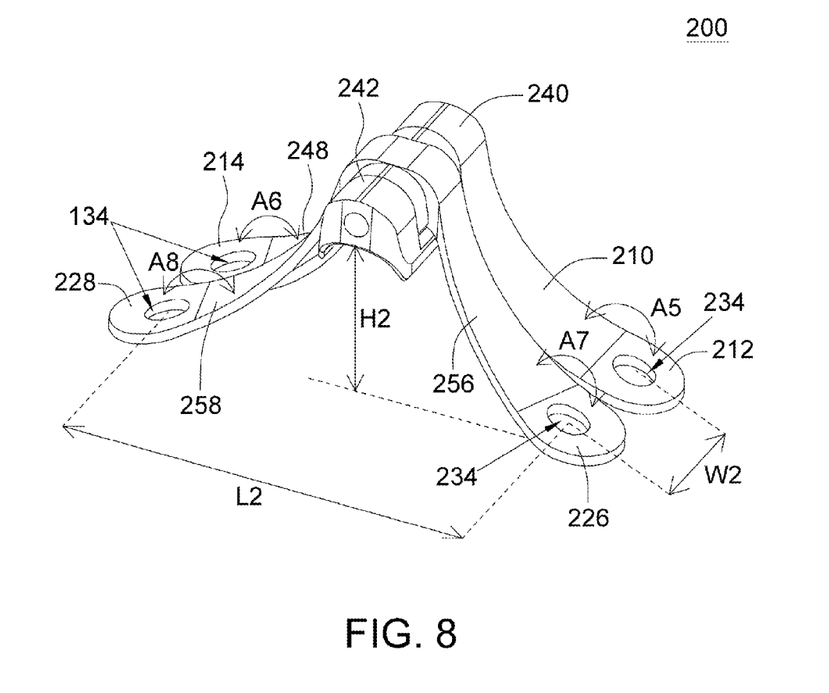
FIG. 8 is a schematic diagram of the scales of the flexible spine fixing structure of FIG. 3.

Referring to FIG. 8, a schematic diagram of the scales of the flexible spine fixing structure of FIG. 3 is shown. Each of the first flexible part 210, the second flexible part 248, the third flexible part 256 and the fourth flexible part 258 has a shape of an arc. An included angle A5 between the first fixing part 212 and the first flexible part 210, an included angle A6 between the second fixing part 214 and the second flexible part 248, an included angle A7 between the third fixing part 226 and the third flexible part 256 and an included angle A8 between the fourth fixing part 228 and the fourth flexible part 258 are all obtuse angles. Preferably but not limited thereto, the obtuse angle is between 120 degrees and 150 degrees. By doing so, the first flexible part 210 and the second flexible part 248 can have flexibility.

Besides, taking the third fixing part 226 as an example, the height H2 of the third fixing part 226 relative to the first connecting piece 240 or the second connecting piece 242, the interval W2 between the through hole of the first fixing part 212 and the through hole of the third fixing part 226 and the interval L2 between the through hole of the third fixing part 226 and the through hole of the fourth fixing part 228 can be suitably designed such that the flexible spine fixing structure 200 does not interfere with the vertebra or contact the spinal cord. For example, according to a scale of a normal vertebra, the height H2 is between 0 mm and 25 mm, the interval L2 is between 30 mm and 40 mm, and the interval W2 is between 10 mm and 15 mm.

Although the height H2 is exemplified to be a distance between the third fixing part 226 and the second connecting piece 242 for illustration, the height H2 may also be a height of any fixing part relative to the first connecting piece 240 or the second connecting piece 242.

Moreover, a distance (not shown in the figure) between the through hole 234 of the second fixing part 214 and the through hole 234 of the fourth fixing part 228 is roughly between 10 mm and 15 mm.

Although the interval W2 is exemplified to be a distance between the through hole of the first fixing part 212 and the through hole of the third fixing part 226 for illustration, the interval W2 can also be a distance between the through hole of the second fixing part 214 and the through hole of the fourth fixing part 228.

Furthermore, in addition to a rectangle, the first flexible part 210, the second flexible part 248, the third flexible part 256 and the fourth flexible part 258 can also have a cross-sectional shape of a circle or an ellipse. In this case, the first flexible part 210, the second flexible part 248, the third flexible part 256 and the fourth flexible part 258 can similarly generate suitable deformation after receiving stress.

Moreover, metal wires can be embedded in the flexible parts. For example, in another example, if the first flexible part 210 is made of polytetrafluoroethylene having soft texture, a metal wire (not shown in the figure) can be embedded in the first flexible part 210 to improve rigidity, elasticity and flexibility of the first flexible part 210. Of course, if the second flexible part 248, the third flexible part 256 or the fourth flexible part 258 has soft texture, the above processing can also be done to these flexible parts.

The flexible spine fixing structure disclosed by the above embodiments includes a first flexible element connected to a second flexible element such that the whole spine fixing structure has flexibility. After the flexible spine fixing structure is fixed to the vertebras, the fixed vertebras can still move and thus the patient can still bend his/her body forwards or backwards or turn his/her body left or right to have a higher mobility and lower discomfort after surgery and the spine degeneration can be avoided.

While the disclosure has been described by way of example and in terms of the exemplary embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A flexible spine fixing structure for fixing to a first vertebra and a second vertebra, comprising:
  a first flexible element, comprising a first connecting part, a first flexible part, a second flexible part, a first fixing part and a second fixing part, wherein one end of the first flexible part and one end of the second flexible part are connected to two opposite ends of the first connecting part respectively, the first fixing part and the second fixing part are connected to the other end of the first flexible part and the other end of the second flexible part respectively and used for fixing to the second vertebra, the first connecting part has an indent;
  a second flexible element, comprising a second connecting part, a third flexible part, a fourth flexible part, a third fixing part and a fourth fixing part, wherein one end of the third flexible part and one end of the fourth flexible part are connected to two opposite ends of the second connecting part respectively, the third fixing part and the fourth fixing part are connected to the other end of the third flexible part and the other end of the fourth flexible part respectively and used for fixing to the first vertebra, the second connecting part has a first through hole; and
  a shaft, disposed by penetrating the indent and the first through hole;
  wherein the first connecting part comprises a first connecting piece, a second connecting piece, a first beam and a second beam, the first beam connecting to the first connecting piece and the second connecting piece, the second beam is disposed in parallel to the first beam and connected to the first connecting piece and the second connecting piece;
  wherein the indent, the first flexible part and the second flexible part are formed on the first connecting piece, the second connecting piece has a second through hole, the shaft penetrates the second through hole, and the second connecting part is disposed between the first connecting piece and the second connecting piece.

2. The flexible spine fixing structure according to claim 1, wherein an included angle between the first fixing part and the first flexible part, an included angle between the second fixing part and the second flexible part, an included angle between the third fixing part and the third flexible part and an included angle between the fourth fixing part and the fourth flexible part are all obtuse angles.

3. The flexible spine fixing structure according to claim 1, wherein an included angle between the first fixing part and the first flexible part, an included angle between the second fixing part and the second flexible part, an included angle between the third fixing part and the third flexible part and an included angle between the fourth fixing part and the fourth flexible part range between 120 and 150 degrees.

4. The flexible spine fixing structure according to claim 1, wherein each of the first flexible part, the second flexible part, the third flexible part and the fourth flexible part has a shape of an arc, the distance between the first connecting part and at least one of the first fixing part, the second fixing part, the third fixing part and the fourth fixing part ranges between 0 mm and 25 mm.

5. The flexible spine fixing structure according to claim 1, wherein the shaft is a flexible shaft.

6. The flexible spine fixing structure according to claim 1, wherein the indent is a blind hole or a through hole, and an outer diameter of the shaft is larger than an inner diameter of one of the first through hole and the indent.

7. The flexible spine fixing structure according to claim 1, wherein the indent is a blind hole or a through hole, an outer diameter of the shaft is larger than an inner diameter of one of the first through hole, the second through hole and the indent.

8. The flexible spine fixing structure according to claim 1, wherein the first beam has a first side surface opposite to the third flexible part, and the second beam has a second side surface opposite to the fourth flexible part;

Wherein the first side surface is separated from the third flexible part by a first interval, and the second side surface is separated from the fourth flexible part by a second interval.

9. The flexible spine fixing structure according to claim 1, wherein the first connecting part is separated from the second connecting part by a third interval, the flexible spine fixing structure further comprises:
a spacer, disposed in the third interval for fixing a relative motion between the first connecting part and the second connecting part.

10. The flexible spine fixing structure according to claim 9, wherein the spacer has a third through hole and the shaft is disposed by further penetrating the third through hole.

11. The flexible spine fixing structure according to claim 1, wherein each of the first fixing part, the second fixing part, the third fixing part and the fourth fixing part has a through hole.

12. The flexible spine fixing structure according to claim 1, wherein each of the first fixing part, the second fixing part, the third fixing part and the fourth fixing part is a board having an through hole.

13. The flexible spine fixing structure according to claim 1, wherein each of the first flexible part, the second flexible part, the third flexible part and the fourth flexible part has a cross-sectional shape of a rectangle, a circle or an ellipse.

14. The flexible spine fixing structure according to claim 1, further comprising:
at least one metal wire embedded in at least one of the first flexible part, the second flexible part, the third flexible part and the fourth flexible part.

15. The flexible spine fixing structure according to claim 1, wherein the first connecting part, the first flexible part, the second flexible part, the first fixing part, and the second fixing part are integrally formed in one piece, the second connecting part, the third flexible part, the fourth flexible part, the third fixing part and the fourth fixing part are integrally formed in one piece.

* * * * *